US008765801B2

(12) United States Patent
Hagen et al.

(10) Patent No.: US 8,765,801 B2
(45) Date of Patent: Jul. 1, 2014

(54) POLYMORPHS OF AZABICYCLOHEXANE

(75) Inventors: Eric J. Hagen, Lafayette, IN (US); Kevin Halloran, Somerset, NJ (US)

(73) Assignee: Euthymics Bioscience, Inc.MA (US)

( * ) Notice: Subject to any disclaimer, the term of this patent is extended or adjusted under 35 U.S.C. 154(b) by 0 days.

(21) Appl. No.: 13/366,209

(22) Filed: Feb. 3, 2012

(65) Prior Publication Data
US 2012/0136038 A1 May 31, 2012

Related U.S. Application Data

(63) Continuation of application No. 13/207,144, filed on Aug. 10, 2011, now abandoned, which is a continuation of application No. 12/428,399, filed on Apr. 22, 2009, now abandoned, which is a continuation of application No. 12/208,284, filed on Sep. 10, 2008, now abandoned, which is a continuation of application No. 11/205,956, filed on Aug. 16, 2005, now abandoned.

(60) Provisional application No. 60/651,505, filed on Aug. 18, 2004.

(51) Int. Cl.
C07D 209/94 (2006.01)
C07D 209/52 (2006.01)
A61K 31/403 (2006.01)
A61P 25/24 (2006.01)

(52) U.S. Cl.
USPC .......................................... 514/412; 548/515

(58) Field of Classification Search
None
See application file for complete search history.

(56) References Cited

U.S. PATENT DOCUMENTS

| 3,892,722 | A | 7/1975 | Babitsky et al. |
|---|---|---|---|
| 4,022,652 | A | 5/1977 | Hirano et al. |
| 4,088,652 | A | 5/1978 | Fanshawe et al. |
| 4,118,393 | A | 10/1978 | Fanshawe et al. |
| 4,118,417 | A | 10/1978 | Epstein |
| 4,131,611 | A | 12/1978 | Fanshawe et al. |
| 4,196,120 | A | 4/1980 | Fanshawe et al. |
| 4,231,935 | A | 11/1980 | Fanshawe et al. |
| 4,336,268 | A | 6/1982 | Bruderer et al. |
| 4,435,419 | A | 3/1984 | Epstein et al. |
| 4,467,102 | A | 8/1984 | Toda et al. |
| 4,504,657 | A | 3/1985 | Bouzard et al. |
| 4,521,431 | A | 6/1985 | Crookes |
| 4,591,598 | A | 5/1986 | Urbach et al. |
| 5,039,680 | A | 8/1991 | Imperato et al. |
| 5,075,431 | A | 12/1991 | Shively et al. |
| 5,130,430 | A | 7/1992 | Shaw |
| 5,198,459 | A | 3/1993 | Imperato et al. |
| 5,232,934 | A | 8/1993 | Downs |
| 5,488,056 | A | 1/1996 | Bodick et al. |
| 5,556,837 | A | 9/1996 | Nester et al. |
| 5,556,838 | A | 9/1996 | Mayer et al. |
| 5,574,052 | A | 11/1996 | Rose et al. |
| 5,663,343 | A | 9/1997 | van der Meij et al. |
| 5,672,360 | A | 9/1997 | Sackler et al. |
| 5,762,925 | A | 6/1998 | Sagen |
| 5,911,992 | A | 6/1999 | Braswell et al. |
| 5,916,920 | A | 6/1999 | Fernandez et al. |
| 5,969,156 | A | 10/1999 | Briggs et al. |
| 5,985,864 | A | 11/1999 | Imai et al. |
| 6,109,269 | A | 8/2000 | Rise et al. |
| 6,121,261 | A | 9/2000 | Glatt et al. |
| 6,194,000 | B1 | 2/2001 | Smith et al. |
| 6,204,284 | B1 | 3/2001 | Beer et al. |
| 6,245,357 | B1 | 6/2001 | Edgren et al. |
| 6,245,911 | B1 | 6/2001 | Imai et al. |
| 6,268,507 | B1 | 7/2001 | Massey et al. |
| 6,333,428 | B1 | 12/2001 | Nakazato et al. |
| 6,372,919 | B1 | 4/2002 | Lippa et al. |
| 6,569,887 | B2 | 5/2003 | Lippa et al. |
| 6,716,868 | B2 | 4/2004 | Lippa et al. |
| 7,041,835 | B2 | 5/2006 | Lippa et al. |
| 7,081,471 | B2 | 7/2006 | Lippa et al. |
| 7,094,799 | B2 | 8/2006 | Russell et al. |
| 7,098,229 | B2 | 8/2006 | Lippa et al. |
| 7,098,230 | B2 | 8/2006 | Lippa et al. |
| 2004/0102638 | A1 | 5/2004 | Russell et al. |
| 2004/0122017 | A1 | 6/2004 | Clader et al. |
| 2004/0127541 | A1 | 7/2004 | Codd et al. |
| 2004/0132797 | A1 | 7/2004 | Lippa et al. |
| 2004/0157869 | A1 | 8/2004 | Lippa et al. |
| 2004/0157870 | A1 | 8/2004 | Lippa et al. |

(Continued)

FOREIGN PATENT DOCUMENTS

AU 519620 B2 12/1981
BE 858683 3/1978

(Continued)

OTHER PUBLICATIONS

Brittain et al. "Effects of pharmaceutical processing on drug polymorphs and solvates" in Polymorphism in Pharmaceutical Solids. vol. 95. p. 331-361 (1990).*
Express-Pharma-Online (http://www.expresspharmaonline.com/20031023/editO2.shtml) 2003.*
Baldessarini, R., "Drugs and the Treatment of Psychiatric Disorders" in Goodman and Gilman's the Pharmacological Basis of Therapeutics, Ninth Edition, J. Hardman et al., Eds., McGraw-Hill, New York, 1996, p. 399 and Chapter 18, pp. 431-459.
Bayes, M. et al., "Gateways to Clinical Trials," Methods and Findings in Experimental and Clinical Pharmacology, 2003, 25 (3), 225-248.
Beer, B. et al., "DOV 216,303, a 'Triple' Reuptake Inhibitor: Safety, Tolerability, and Pharmacokinetic Profile," The Journal of Clinical Pharmacology, 2004, 44 (12), 1360-1367.

(Continued)

Primary Examiner — Sun Jae Yoo
(74) Attorney, Agent, or Firm — Hoxie & Associates LLC

(57) ABSTRACT

The invention provides polymorphic crystalline forms of acid addition salts of (+)-1-(3,4-dichlorophenyl)-3-azabicyclo [3.1.0]hexane designated as polymorph form A, polymorph form B and polymorph form C, where polymorph form A is more thermodynamically stable than the other forms, methods for preparing and using such polymorph forms and pharmaceutical compositions containing such polymorph forms.

1 Claim, No Drawings

(56) References Cited

U.S. PATENT DOCUMENTS

| | | | |
|---|---|---|---|
| 2004/0157908 A1 | 8/2004 | Lippa et al. | |
| 2006/0223875 A1 | 10/2006 | Skolnick et al. | |
| 2008/0269348 A1 | 10/2008 | Skolnick et al. | |
| 2008/0293822 A1 | 11/2008 | Skolnick et al. | |

FOREIGN PATENT DOCUMENTS

| | | |
|---|---|---|
| BE | 893707 | 12/1982 |
| EP | 0 444 855 A1 | 9/1991 |
| JP | 58-13568 A | 1/1983 |
| JP | 4-211638 A | 8/1992 |
| JP | 9-183779 A | 7/1997 |
| JP | 2000-159761 A | 6/2000 |
| JP | 2000-256384 A | 9/2000 |
| JP | 2000-336071 A | 12/2000 |
| WO | WO 99/49857 A1 | 10/1999 |
| WO | WO 03/047568 | 6/2003 |
| WO | WO 2005/080382 | 9/2005 |
| WO | WO 2006/023659 | 3/2006 |
| WO | WO 2006/096810 | 9/2006 |
| WO | WO 2006/108701 | 10/2006 |
| WO | WO 2007/016155 | 2/2007 |
| WO | WO 2007/022933 | 3/2007 |
| WO | WO 2007/022934 | 3/2007 |
| WO | WO 2007/022980 | 3/2007 |

OTHER PUBLICATIONS

Bernstein, J., "Crystal Structure Prediction and Polymorphism," ACA Transactions, 2004, 39, 14-23.
Blum, K. et al., "Dopamine D2 Receptor Gene Variants: Association and Linkage Studies in Impulsive-Addictive-Compulsive Behaviour," Pharmacogenetics, 1995, 5 (3), 121-141.
Braga, D. et al., "Dealing with Crystal Forms (the Kingdom of Serendip?)," Chemistry, an Asian Journal, 2011, 6, 2214-2223.
Bray, G., "A Concise Review on the Therapeutics of Obesity," Nutrition, 2000, 16 (10), 953-960.
Brittain, H., Ed., Polymorphism in Pharmaceutical Solids, 1999, p. 238.
Brittain, H., Ed., "Effects of Pharmaceutical Processing on Drug Polymorphs and Solvates" in Polymorphism in Pharmaceutical Solids, 1990, 95, 331-361.
Caira, M., "Crystalline Polymorphism of Organic Compounds," Topics in Current Chemistry, 1998, 198, 163-208.
Casadio, S. et al., "Acide Phenyl-1-Hydroxymethyl-2-Cyclopropane Carboxylique Et Derives," Bollettino Chimico Farmaceutico, 1978, 117, 331-342.
Chawla, G. et al., "Challenges in Polymorphism of Pharmaceuticals," CRIPS, 2004, 5 (1), 4 pages.
Concise Encyclopedia Chemistry, Walter de Gruyter and Company, Berlin; New York, 1993.
Crown, W., "Economic Outcomes Associated with Tricyclic Antidepressant and Selective Serotonin Reuptake Inhibitor Treatments for Depression," Acta Psychiatrica Scandinavica Supplementum, 2000, 403, 62-66.
Czobor, P., "A Two Center Double-Blind Placebo-Controlled Randomized Study of DOV 220,075 (Bicifadine) SR and Tramadol 100 mg in the Treatment of Post-Operative Dental Pain," American Pain Society, 2003, Abstract (801).
Czobor, P., "A Double-Blind, Placebo Controlled Randomized Study of DOV 220,075 (Bicifadine) SR and Codeine 60 mg in the Treatment of Post-Operative Dental Pain," American Pain Society 2003, Abstract (915).
D'Aquila, P. et al., "The Role of Dopamine in the Mechanism of Action of Antidepressant Drugs," European Journal of Pharmacology, 2000, 405 (1-3), 365-373.
Dunitz, J., "Are Crystal Structures Predictable," Chemical Communications, 2003, 545-548.
English-language abstract for JP 2000-159761 from the European Patent Office website (http://worldwide.espacenet.com/ publicationDetails/biblio?DB=EPODOC&II=1&ND=3& adjacent=true&locale=en_EP&FT=D&date=20000613&CC=JP& NR=2000159761A&KC=A), 2 pages, website accessed Jan. 14, 2014.
English-language abstract for JP 2000-256384 A from the European Patent Office website (http://worldwide.espacenet.com/ publicationDetails/biblio?DB=EPODOC&II=1&ND=3& adjacent=true&locale=en_EP&FT=D&date=20000919&CC=JP& NR=2000256384A&KC=A), 2 pages, website accessed Jan. 14, 2014.
Epstein, J. et al., "1-Aryl-3-azabicyclo[3.1.0]hexanes, a New Series of Nonnarcotic Analgesic Agents," Journal of Medicinal Chemistry, 1981, 24 (5), 481-490.
Epstein, J. et al., "Bicifadine: Non-Narcotic Analgesic Activity of 1-Aryl-3-Azabicycl[3.1.0]Hexanes," NIDA Research Monograph, 1982, 41, 93-98.
Ettmayer, P. et al., "Lessons Learned from Marketed and Investigational Prodrugs," Journal of Medicinal Chemistry, 2004, 47 (10), 2393-2404.
Express-Pharma-Online, http://www.expresspharmaonline.com/ 20031023/edit02.shtml, 2013.
Fauci, A. et al., Eds., Harrison's Principles of Internal Medicine, Fourteenth Edition, 1998, pp. 2485-2503.
Frazer, A. "Norepinephrine Involvement in Antidepressant Action," Journal of Clinical Psychiatry, 2000, 61 (Suppl. 10), 25-30.
Fredman, S. et al., "Partial Response, Nonresponse, and Relapse with Selective Serotonin Reuptake Inhibitors in Major Depression: A Survey of Current 'Next-Step' Practices," Journal of Clinical Psychiatry, 2000, 61 (6), 403-408.
Grant, J., Ed., Hackh's Chemical Dictionary, Fourth Edition, McGraw-Hill Book Company, New York, 1969, pp. 474-475.
Hitri, A. et al., "Molecular, Functional and Biochemical Characteristics of the Dopamine Transporter: Regional Differences and Clinical Relevance," Clinical Neuropharmacology, 1994, 17 (1), 1-22.
Hoffman, B. et al., "Localization and Dynamic Regulation of Biogenic Amine Transporters in the Mammalian Central Nervous System," Frontiers in Neuroendocrinology, 1998, 19 (3), 187-231.
International Search Report for International Patent Application No. PCT/US2005/029420, mailed Sep. 25, 2006, 2 pages.
International Preliminary Report on Patentability for International Patent Application No. PCT/US2005/029420, Date of issuance of the report Feb. 20, 2007, 4 pages.
Kiyatkin, E., "Dopamine Mechanisms of Cocaine Addiction," The International Journal of Neuroscience, 1994, 78 (1-2), 75-101.
Kreek, M., "Cocaine, Dopamine and the Endogenous Opiod System," Journal of Addictive Diseases, 1996, 15 (14), 73-96.
Leonhardt, M. et al., "New Approaches in the Pharmacological Treatment of Obesity," European Journal of Nutrition, 1999, 38 (1), 1-13.
Lima, L. et al., "Bioisosterism: A Useful Strategy for Molecular Modification and Drug Design," Current Medicinal Chemistry, 2005, 12 (1), 23-49.
Maddox, J., "Crystals from First Principles," Nature, 1988, 335, 201.
McArdle, P. et al., "A Method for the Prediction of the Crystal Structure of Ionic Organic Compounds—The Crystal Structures of O-Toluidinium Chloride and Bromide and Polymorphism of Bicifadine Hydrochloride," CrystEngComm, 2004, 6 (53), 303-309.
McBriar, M. et al., "Discovery of Bicycloalkyl Urea Melanin Concentrating Hormone Receptor Antagonists: Orally Efficacious Antiobesity Therapeutics," Journal of Medicinal Chemistry, 2005, 48 (7), 2274-2277.
McBriar, M. et al., "Discovery of Orally Efficacious Melanin-Concentrating Hormone Receptor01 Antagonists as Antiobesity Agents. Synthesis, SAR, and Biological Evaluation of Bicyclo[3.1.0]hexyl Ureas," Journal of Medicinal Chemistry, 2006, 49 (7), 2294-2310.
McMillen, B. et al., "Effect of DOV 102,677 on the Volitional Consumption of Ethanol by Myers' High Ethanol-Preferring Rat," Alcoholism, Clinical and Experimental Research, 2007, 31 (11), 1866-1871.
Meyerson, L. et al., "Allosteric Interaction Between the Site Labeled by [$^3$H]Imipramine and the Serotonin Transporter in Human Platelets," Journal of Neurochemistry, 1987, 48 (2), 560-565.
Micheli, F. et al., "1-(Aryl)-6-[alkoxyalkyl]-3-azabicyclo[3.1.0]hexanes and 6-(Aryl)-6-[alkoxyalkyl]-3-azabicyclo[3.1.

(56) References Cited

OTHER PUBLICATIONS

0]hexanes: A New Series of Potent and Selective Triple Reuptake Inhibitors," Journal of Medicinal Chemistry, 2010, 53 (6), 2534-2551.

Morissette, S. et al., "High-Throughput Crystallization: Polymorphs, Salts, Co-Crystals and Solvates of Pharmaceutical Solids," Advanced Drug Delivery Reviews, 2004, 56 (3), 275-300.

Nagatsu, T. et al., "Changes in Cytokines and Neurotrophins in Parkinson's Disease," Journal of Neural Transmission. Supplementa, 2000, 60, 277-290.

Newman, A. et al., "Solid-State Analysis of the Active Pharmaceutical Ingredient in Drug Products," Drug Discovery Today, 2003, 8 (19), 898-905.

Noble, E., "Polymorphisms of the D2 Dopamine Receptor Gene and Alcoholism and Other Substance Use Disorders," Alcohol and Alcoholism—Supplements, 1994, 2, 35-43.

"Pain Therapeutics Takes Different Path, Improving Long-term Pain Relief by Reducing Dependency and Tolerance," Genetic Engineering and Biotechnology News, 2006, 26 (12).

Porter, E., "Single Dose Comparison of Bicifadine, Codeine, and Placebo in Postoperative Pain," Current Therapeutic Research, 1981, 30 (3), 156-160.

Price, S., "The Computational Prediction of Pharmaceutical Crystal Structures and Polymorphism," Advanced Drug Delivery Reviews, 2004, 56, 301-319.

Rouhi, A., "The Right Stuff, From Research and Development to the Clinic, Getting Drug Crystals Right is Full of Pitfalls," Chemical and Engineering News, 2003, 81 (8), 32-35.

Scates, A. et al., "Reboxetine: A Selective Norepinephrine Reuptake Inhibitor for the Treatment of Depression," The Annals of Pharmacotherapy, 2000, 34 (11), 1302-1312.

Shuto, S. et al., "Synthesis of (+)- and (−)-Milnaciprans and Their Conformationally Restricted Analogs," Tetrahedron Letters, 1996, 37 (5), 641-644.

Simon, G. et al., "TCAs or SSRIs As Initial Therapy for Depression," Journal of Family Practice, 1999, 48, 845-846.

Skolnick, P., "Beyond Monoamine-Based Therapies: Clues to New Approaches," Journal of Clinical Psychiatry, 2002, 63 (Suppl. 2), 19-23.

Skolnick, P. et al., "Antidepressant-like Actions of DOV 21,947, A 'Triple' Uptake Inhibitor," European Journal of Pharmacology, 2003, 461, 99-104.

Skolnick, P. et al., "'Broad Spectrum' Antidepressants: Is More Better for the Treatment of Depression," Life Sciences, 2003, 73 (25), 3175-3179.

Stacy, M. et al., "Treatment Options for Early Parkinson's Disease," American Family Physician, 1996, 53 (4), 1281-1287.

Stella, V., "Prodrugs as Therapeutics," Expert Opinion on Therapeutic Patents, 2004, 14 (3), 277-280.

Sullivan, A. et al., "Mechanisms of Appetite Modulation by Drugs," Federation Proceedings, 1985, 44 (1 Pt. 1), 139-144.

Taylor, A. et al., "Scales for the Identification of Adults with Attention Deficit Hyperactivity Disorder (ADHD): A Systematic Review," Research in Developmental Disabilities, 2011, 32 (3), 924-938.

Testa, B., "Prodrug Research: Futile or Fertile," Biochemical Pharmacology, 2004, 68 (11), 2097-2106.

Theeuwes, F., "Drug Delivery Fuels Specialty Pharma, Rich Source of Innovation Now Significant Platform to Launch New Companies," Genetic Engineering and Biotechnology News, 2007, 27 (10).

U.S. Pharmacopia #23, National Formulary #18, 1995, pp. 1843-1844.

Vippagunta, S. et al., "Crystalline Solids," Advanced Drug Delivery Reviews, 2001, 48 (1), 3-26.

Vishweshwar, P. et al., "The Predictably Elusive Form II of Aspirin," Journal of the American Chemical Society, 2005, 127, 16802-16803.

Wang, R. et al., "The Oral Analgesic Efficacy of Bicifadine Hydrochloride in Postoperative Pain," The Journal of Clinical Pharmacology, 1982, 22 (4), 160-164.

Welch, W., "Nontricyclic Antidepressant Agents Derived from cis- and trans-1-Amino-4-aryltetralins," Journal of Medicinal Chemistry, 1984, 27, 1508-1515.

Wolff, M., Ed., Burger's Medicinal Chemistry, Fifth Edition, vol. 1, pp. 975-977, 2013.

Wong, E. et al., "Reboxetine: A Pharmacologically Potent, Selective, and Specific Norepinephrine Reuptake Inhibitor," Biological Psychiatry, 2000, 47 (9), 818-829.

Xu, F. et al., "Stereocontrolled Synthesis of Trisubstituted Cyclopropanes: Expedient, Atom-Economical, Asymmetric Syntheses of (+)-Bicifadine and DOV21947," Organic Letters, 2006, 8 (17), 3885-3888.

Zhang, M. et al., "Studies on the Structure-Activity Relationship of Bicifadine Analogs as Monoamine Transporter Inhibitors," Bioorganic and Chemistry Letters, 2008, 18 (13), 3682-3686.

\* cited by examiner

POLYMORPHS OF AZABICYCLOHEXANE

This application claims priority as a CONTINUATION of prior application U.S. patent application Ser. No. 13/207,144, filed Aug. 10, 2011, which is a continuation of U.S. patent application Ser. No. 12/428,399, filed Apr. 22, 2009, which is a continuation of U.S. patent application Ser. No. 12/208,284, filed Sep. 10, 2008, which is a continuation of U.S. patent application Ser. No. 11/205,956, filed Aug. 16, 2005, which claims the benefit of U.S. patent application Ser. No. 10/920,748, filed Aug. 18, 2004, which was converted to U.S. Provisional Application No. 60/651,505, the disclosure of which priority is claimed and incorporated herein in their entirety by reference.

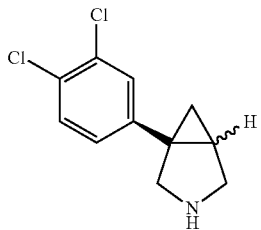

are known for use in treating depression. As set forth in Lippa et al., U.S. Pat. No. 6,372,919, the compound of formula I whose chemical name is (+)-1-(3,4-dichlorophenyl)-3-azabicyclo[3.1.0]hexane in its (+) isomeric form has been found to have potent anti-depressive activity.

While the azabicyclohexanes of formula I have been prepared as described in various U.S. patents such as U.S. Pat. Nos. 4,231,935, 4,131,611, 4,435,419, 4,118,417 and 4,196,120, these compounds were prepared in racemic form. In the procedure of Lippa et al., U.S. Pat. No. 6,372,919, the (+) optical antipode was produced as a mixture of various isomeric polymorphic forms which heretofore have been unrecognized. A pure crystalline form of the (+) isomer of the compound of formula I is of particular importance since it could be formulated into various pharmaceutical dosage forms such as for example tablets or capsules for treatment of patients. Variations in crystal structure of a pharmaceutical drug substance are known to affect the dissolution, manufacture, stability and bioavailability of a pharmaceutical drug product, particularly in solid oral dosage forms. Therefore it is important to produce the (+) isomer of the compound of formula I in a pure form comprising a single thermodynamically stable crystal structure.

SUMMARY OF INVENTION

In accordance with this invention, it has been discovered that the (+) optical antipode of the compound of formula I as prepared in Lippa et al., U.S. Pat. No. 6,372,919 exists as a mixture of two crystalline polymorphic structures, one being the hemi-hydrate form, which is designated as polymorph form A, and the other being the anhydrous form, which is designated as polymorph form B. A dehydrated form designated as polymorph form C has also been found. When the (+) optical antipode of the compound of formula I is produced by prior art procedures, it has been found that it was produced as a mixture of polymorph form A and polymorph form B which do not readily separate into their pure polymorphic crystalline forms.

In accordance with this invention, a method of forming these polymorphs as pure independent polymorph forms has been discovered. In addition we have found that the polymorph form A of the (+) optical antipode of the compound of formula I in its pure crystalline structure produced in accordance with this invention is a thermodynamically stable polymorph form. Therefore, form A is the preferred crystalline form of the (+) optical antipode of the acid addition salt of the compound of formula I for formulation into pharmaceutical drug products.

DETAILED DESCRIPTION OF THE INVENTION

In accordance with this invention, it has been discovered that the (+) optical antipode of acid addition salts of the compound of formula I exists in three different crystalline polymorphic forms designated as polymorph form A, polymorph form B and polymorph form C and that polymorph form A, which is the hemi-hydrate form, is a thermodynamically stable form.

Polymorph form A may be characterized as the hemi-hydrate of acid addition salts of (+)-1-(3,4-dichlorophenyl)-3-azabicyclo[3.1.0]hexane. It is the hemi-hydrate crystalline form, which uniquely characterizes polymorph form A from polymorph form B and polymorph form C of acid addition salts of the compound of formula I. Polymorph form B and polymorph form C of acid addition salts of (+)-1-(3,4-dichlorophenyl)-3-azabicyclo[3.1.0]hexane do not exist as hemi-hydrates.

The polymorphs of acid addition salts of (+)-1-(3,4-dichlorophenyl)-3-azabicyclo[3.1.0]hexane may also be characterized by their X-ray powder diffraction patterns (XRPD) and/or their Raman spectroscopy peaks. With respect to X-ray powder diffraction, the relative intensities of the X-ray powder diffraction peaks of a given polymorph may vary depending upon the crystal size of the polymorph used to determine the pattern. This is a phenomenon of preferred orientation. Preferred orientation is caused by the morphology of crystals. In this case, the XRPD analysis should be carried out with the sample spinning in the sample holder during XRPD analysis to reduce the preferred orientation effects. Samples for XPRD analysis for determination of the presence and nature of their polymorph status in accordance with this invention should be lightly ground and/or sieved to a crystal size of from about 10 to 40 microns for XPRD analysis.

A Bragg-Brentano instrument, which includes the Shimadzu system, used for the X-ray powder diffraction pattern measurements reported herein, gives a systematic peak shift (all peaks can be shifted at a given "°2θ" angle) which result from sample preparation errors as described in Chen et al.; J Pharmaceutical and Biomedical Analysis, 2001; 26, 63. Therefore, any "°2θ" angle reading of a peak value is subject to an error of about (±) 0.2°.

The X-ray powder diffraction pattern (XRPD) analyses of polymorph forms A, B and C were performed with a Shimadzu XRD-6000 X-ray powder diffractometer using Cu Kα radiation. In this procedure the compound as a hydrochloride salt was loaded onto the machine as a crystalline powder. The instrument was equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40 °2θ was used. A silicon standard was analyzed to check the instrument alignment. Data were collected and analyzed using XRD-6000 v. 4.1.

The following Table 1 shows the peaks of the X-ray powder diffraction pattern of purified polymorph form A of the hydrochloride salt of (+)-1-(3,4-dichlorophenyl)-3-azabicyclo [3.1.0]hexane having a crystal size of from about 10 to 40 microns. This pattern is given in terms of the "°2θ" angles of the peaks subject to the angle error set forth above. With respect to the percent value of relative intensity (I/Io) given in Table 1, Io represents the value of the maximum peak determined by XRPD for the sample for all "°2θ" angles and I represents the value for the intensity of a peak measured at a given "°2θ" angle". The angle "°2θ" is a diffraction angle which is the angle between the incident X-rays and the diffracted X-rays. The values for the relative intensities for a given peak set forth in percent and the "°2θ" angles where said peaks occur are given in Table 1 below.

TABLE 1

XRPD Peaks (°2θ) and Relative Intensities (I/Io) for Polymorph Form A
Form A

| °2θ | I/Io |
|---|---|
| 4.55 | 25 |
| 9.10 | 15 |
| 13.65 | 6 |
| 17.14 | 60 |
| 17.85 | 11 |
| 18.24 | 23 |
| 18.49 | 14 |
| 19.27 | 14 |
| 19.62 | 22 |
| 21.74 | 15 |
| 21.96 | 100 |
| 22.24 | 12 |
| 23.01 | 7 |
| 24.52 | 43 |
| 24.79 | 10 |
| 26.74 | 52 |
| 27.44 | 11 |
| 27.63 | 17 |
| 28.36 | 16 |
| 28.48 | 26 |
| 29.00 | 14 |
| 29.20 | 19 |
| 29.40 | 27 |
| 29.57 | 27 |
| 30.24 | 18 |
| 31.01 | 13 |
| 31.62 | 17 |
| 32.20 | 24 |
| 32.93 | 12 |
| 33.42 | 9 |
| 34.24 | 6 |
| 35.08 | 15 |
| 35.65 | 16 |
| 36.31 | 14 |
| 37.11 | 26 |
| 37.78 | 9 |
| 39.85 | 9 |

The following Table 2 shows the peaks of the X-ray powder diffraction pattern of purified polymorph form B of the hydrochloride salt of (+)-1-(3,4-dichlorophenyl)-3-azabicyclo [3.1.0]hexane having a crystal size of from about 10 to 40 microns. The values for the relative intensities for a given peak set forth in percent and the "°2θ" angles where said peaks occur for polymorph form B of the hydrochloride salt of (+)-1-(3,4-dichlorophenyl)-3-azabicyclo[3.1.0]hexane having a crystal size of about 10 to 40 microns are given in Table 2 below.

TABLE 2

XRPD Peaks (°2θ) and Relative Intensities (I/Io) for Polymorph Form B
Form B

| °2θ | I/Io |
|---|---|
| 10.50 | 6 |
| 13.34 | 12 |
| 15.58 | 42 |
| 17.12 | 6 |
| 17.36 | 8 |
| 17.52 | 26 |
| 18.21 | 11 |
| 20.40 | 7 |
| 21.35 | 97 |
| 21.61 | 17 |
| 21.93 | 11 |
| 22.64 | 6 |
| 23.04 | 79 |
| 24.09 | 6 |
| 24.52 | 14 |
| 25.43 | 96 |
| 26.24 | 53 |
| 26.36 | 73 |
| 26.75 | 11 |
| 26.88 | 7 |
| 27.44 | 6 |
| 27.94 | 12 |
| 28.36 | 20 |
| 28.54 | 30 |
| 29.39 | 10 |
| 29.72 | 9 |
| 30.07 | 7 |
| 30.58 | 8 |
| 30.72 | 100 |
| 31.07 | 14 |
| 31.38 | 12 |
| 31.55 | 7 |
| 31.78 | 12 |
| 32.14 | 10 |
| 32.31 | 7 |
| 32.80 | 7 |
| 32.95 | 6 |
| 33.45 | 44 |
| 33.74 | 12 |
| 35.25 | 10 |
| 35.40 | 12 |
| 35.58 | 9 |
| 36.75 | 8 |
| 37.55 | 18 |
| 39.01 | 15 |
| 39.22 | 7 |
| 39.37 | 7 |
| 39.86 | 11 |

The following Table 3 shows the peaks of the X-ray powder diffraction pattern of purified polymorph form C of the hydrochloride salt of (+)-1-(3,4-dichlorophenyl)-3-azabicyclo [3.1.0]hexane having a crystal size of from about 10 to 40 microns. The values for the relative intensities for a given peak set forth in percent and the "°2θ" angles where said peaks occur for polymorph form C of the hydrochloride salt of (+)-1-(3,4-dichlorophenyl)-3-azabicyclo[3.1.0]hexane having a crystal size of about 10 to 40 microns are given in Table 3 below.

TABLE 3

XRPD Peaks (°2θ) and Relative Intensities (I/Io) for Polymorph Form C
Form C

| °2θ | I/Io |
|---|---|
| 5.46 | 6 |
| 5.66 | 20 |
| 6.37 | 6 |
| 7.26 | 6 |

TABLE 3-continued

XRPD Peaks (°2θ) and Relative Intensities (I/Io) for Polymorph Form C

Form C

| °2θ | I/Io |
|---|---|
| 8.75 | 6 |
| 13.34 | 25 |
| 13.94 | 11 |
| 15.65 | 7 |
| 16.26 | 7 |
| 17.01 | 8 |
| 17.38 | 9 |
| 17.64 | 83 |
| 17.92 | 15 |
| 18.23 | 40 |
| 19.08 | 7 |
| 19.38 | 46 |
| 19.86 | 20 |
| 20.07 | 100 |
| 21.16 | 17 |
| 21.32 | 94 |
| 21.64 | 37 |
| 22.42 | 25 |
| 22.70 | 12 |
| 22.97 | 70 |
| 23.31 | 6 |
| 24.09 | 15 |
| 24.86 | 94 |
| 25.24 | 32 |
| 25.38 | 49 |
| 26.12 | 13 |
| 26.32 | 90 |
| 26.87 | 18 |
| 27.21 | 39 |
| 27.90 | 54 |
| 28.14 | 8 |
| 28.56 | 32 |
| 28.74 | 17 |
| 29.20 | 6 |
| 29.72 | 6 |
| 29.92 | 26 |
| 30.54 | 13 |
| 30.72 | 19 |
| 30.96 | 31 |
| 31.42 | 7 |
| 31.68 | 11 |
| 31.80 | 15 |
| 31.97 | 6 |
| 32.43 | 21 |
| 33.26 | 12 |
| 33.40 | 15 |
| 33.64 | 25 |
| 33.84 | 18 |
| 34.11 | 15 |
| 34.70 | 11 |
| 35.07 | 8 |
| 35.64 | 11 |
| 35.91 | 8 |
| 36.09 | 21 |
| 37.80 | 12 |
| 38.06 | 6 |
| 38.17 | 6 |
| 39.04 | 6 |
| 39.23 | 8 |
| 39.77 | 7 |

However, there are key major peaks at given angles in these X-ray powder diffraction patterns which are unique to each given polymorph form. These peaks are present in the XRPD patterns of each of the polymorph forms having a crystal size of about 10 to 40 microns. Any of these major peaks, either alone or in any distinguishing combination, are sufficient to distinguish one of the polymorph forms from the other two polymorph forms. For polymorph form A, the "°2θ" angles of these major peaks which characterize polymorph form A, subject to the error set forth above, are as follows:

17.14;
19.62;
21.96;
24.52;
and
26.74.

Any of these major peaks, either alone or in any distinguishing combination, are sufficient to distinguish polymorph form A from the other two polymorph forms.

Also, there are key major peaks at given angles in the XRPD of polymorph form B which are unique to polymorph form B as the hydrochloride salt having a crystal size of about 10 to 40 microns that are typically present in the XRPD pattern of polymorph form B as the hydrochloride salt irrespective of the particle size. Any of these major peaks, either alone or in any distinguishing combination, are sufficient to distinguish polymorph form B from the other two polymorph forms. For polymorph form B, the "°2θ" angles of these major peaks which characterize polymorph form B, subject to the error set forth above, are as follows:

15.58;
17.52;
21.35;
23.04;
25.43;
and
30.72.

Also, there are key major peaks at given angles in the XRPD of polymorph form C which are unique to polymorph form C as the hydrochloride salt, having a crystal size of about 10 to 40 microns, that are typically present in the XRPD pattern of polymorph form C as a hydrochloride salt irrespective of the particle size. Any of these major peaks, either alone or in any distinguishing combination, are sufficient to distinguish polymorph form C from the other two polymorph forms. For polymorph form C, the "°2θ" angles of these major peaks which characterize polymorph form C, subject to the error set forth above, are as follows:

13.34;
17.64;
20.07;
21.32;
22.97;
24.86;
26.32;
and
27.90.

Another method of characterizing the three polymorphs of (+)-1-(3,4-dichlorophenyl)-3-azabicyclo[3.1.0]hexane is through Raman spectroscopy. The procedure for carrying out Raman Spectroscopy is described on pages 260-275 of Skoog and West, Principles of Instrumental Analysis (2nd Ed.); Saunders College, Pa. (1980).

Briefly, Raman spectra were obtained using a FT-Raman 960 (or 860) spectrometer (Thermo Nicolet) interfaced to an 860 FT-IR. This spectrometer uses an excitation wavelength of 1064 nm. Approximately 0.912 W of Nd:YV0$_4$ laser power was used to irradiate the samples. The Raman spectra were measured with an indium gallium arsenide (InGaAs) detector. The samples were pressed into pellets for analysis. A total of 128 sample scans were collected from 3600 or 3700-98 cm$^{-1}$ at a spectral resolution of about ($\pm$) 4 cm$^{-1}$, using Happ-Genzel apodization. Wavelength calibration was performed using sulfur and cyclohexane. The Raman spectra peak positions given below in wavenumbers (cm$^{-1}$) for the purified polymorph forms A, B and C of the hydrochloride salt of (+)-1-(3,4-dichlorophenyl)-3-azabicyclo[3.1.0]hexane are subject to an error of about ($\pm$) 4 cm$^{-1}$.

The Raman spectra peak positions in wavenumbers (cm$^{-1}$) for polymorph form A of the hydrochloride salt of (+)-1-(3,4-dichlorophenyl)-3-azabicyclo[3.1.0]hexane are given in Table 4.

TABLE 4

Raman Peak Listing for Polymorph Form A (peaks > 400 cm$^{-1}$)
Peak Positions In Wavenumbers (cm$^{-1}$)
Form A 436
479
534
549
646
691
680
762
812
836
892
921
959
982
998
1030
1056
1099
1122
1135
1189
1229
1274
1309
1338
1366
1393
1453
1484
1557
1597
2890
2969
2982
3017
3046
3064

The Raman spectra peak positions in wavenumbers (cm$^{-1}$) for polymorph form B of the hydrochloride salt of (+)-1(3,4-dichlorophenyl)-3-azabicyclo[3.1.0]hexane are listed in Table 5.

TABLE 5

Raman Peak Listing for Polymorph Form B (peaks > 400 cm$^{-1}$)
Peak Positions In Wavenumbers (cm$^{-1}$)
Form A 418
446
478
533
648
676
686
767
825
852
895
964
979
1031
1054
1070
1099
1136
1189
1245
1278
1309
1343
1380
1398
1456
1483
1557
1593
2895
2963
2993
3027
3066

The Raman spectra peak positions in wavenumbers (cm$^{-1}$) for polymorph form C of the hydrochloride salt of (+)-1-(3,4-dichlorophenyl)-3-azabicyclo[3.1.0]hexane are given in Table 6.

TABLE 6

Raman Peak Listing for Polymorph Form C (peaks > 400 cm$^{-1}$)
Peak Positions In Wavenumbers (cm$^{-1}$)
Form C 441
474
532
648
674
690
767
811
826
856
895
970
1031
1059
1094
1122
1137
1189
1228
1246
1266
1279
1309
1343
1398
1456
1471
1557
1595
2900
2966
2992
3048
3070

Table 4, Table 5 and Table 6 provide the complete patterns of the Raman peak positions with respect to the hydrochloride salts of polymorph forms A, B and C respectively. However, there are certain key peaks, within these patterns, which are unique to each of the hydrochloride salts of these polymorphs. Any of these key peaks, either alone or in any distinguishing combination, are sufficient to distinguish one of the polymorph forms from the other two polymorph forms. These peak positions, expressed in wavenumbers (cm$^{-1}$) for the hydrochloride salt of polymorph form A are:

Peak Positions in Wavenumbers (cm$^{-1}$) for
Polymorph Form A

762;
636;
921;
959;
1393;
1597;
2890;
2982;
and
3064.

Any of these key peaks, either alone or in any distinguishing combination, are sufficient to distinguish polymorph form A from the other two polymorph forms The characterizing peak positions expressed in wavenumbers (cm$^{-1}$) for the hydrochloride salt of polymorph form B are:

Peak Positions in Wavenumbers (cm$^{-1}$) for
Polymorph Form B

1245;
1380;
2963;
2993;
3027;
and
3066.

Any of these key peaks, either alone or in any distinguishing combination, are sufficient to distinguish polymorph form B from the other two polymorph forms.

The characterizing peak positions expressed in wavenumbers (cm$^{-1}$) for the hydrochloride salt of polymorph form C are:

Peak Positions in Wavenumbers (cm$^{-1}$) for
Polymorph Form C

1059;
1094;
1266;
1343;
1595;
2900;
2966;
and
3070.

Any of these key peaks, either alone or in any distinguishing combination, are sufficient to distinguish polymorph form C from the other two polymorph forms In accordance with this invention, each of the crystalline polymorph forms of the acid addition salt (+)-1-(3,4-dichlorophenyl)-3-azabicyclo[3.1.0]hexane can be obtained substantially free of its other enantiomeric, geometric and polymorphic isomeric forms. The term "substantially free" of its other enantiomeric, geometric and polymorphic isomeric forms designates that the crystalline material is at least about 95% by weight pure in that it contains no more than about 5% w/w of its other enantiomeric, geometric and polymorphic isomeric forms.

In the past, preparation of acid addition salts of (+)-1-(3,4-dichlorophenyl)-3-azabicyclo[3.1.0]hexane has resulted in a mixture of the A and B polymorph forms. This mixture constituted an approximately 50% by weight mixture of each polymorph which could not be easily separated. In addition, it has been found that there was some inter-conversion of polymorph forms A and B upon standing at ambient temperature or inter-conversion, upon heating, of this 50% mixture to form a mixture of polymorph forms A, B and C. However, these mixtures could not be easily separated. Therefore, the purified isomeric forms of these individual polymorph forms substantially free of its other enantiomeric, geometric and polymorphic isomeric forms could not be obtained.

In accordance with this invention, it has been discovered that polymorph forms A, B and C of (+)-1-(3,4-dichlorophenyl)-3-azabicyclo[3.1.0]hexane, particularly as hydrochloride acid addition salts, can each be prepared substantially free of its other enantiomeric, geometric and polymorphic isomeric forms through re-crystallization of a mixture of the A and B polymorph forms produced in accordance with prior art procedures. Depending upon the particular solvent, conditions and concentrations of materials utilized to re-crystallize the mixture of polymorph forms A and B, one can selectively produce the desired polymorph form of (+)-1-(3,4-dichlorophenyl)-3-azabicyclo[3.1.0]hexane, substantially free of its other enatiomeric, geometric and polymorphic isomers.

In preparing polymorph forms A and B substantially free of other polymorph forms, crystallization from a mixture of A and B is generally utilized. However, the crystallization technique with regard to producing each of these polymorph forms substantially free of other polymorph forms is different. In preparing polymorph form A, which is the hemihydrate of the acid addition salt of (+)-1-(3,4-dichlorophenyl)-3-azabicyclo[3.1.0]hexane, it is best to utilize a solvent medium to dissolve a solid containing polymorph form A such as a mixture of polymorph forms A and B in an organic solvent which contains water. The preferred organic solvents that can be utilized in this procedure include lower alkanol solvents such as methanol, butanol, ethanol or isopropanol as well as other solvents such as acetone, dichloromethane and tetrahydrofuran. In forming the purified polymorph form A substantially free of other polymorph forms, it is best to incorporate water in these solvents when preparing the medium for crystallization. Once the solid, preferably a mixture of polymorph forms A and B, is dissolved in this medium, the solvent should be allowed to evaporate at room temperature over a long period of time while the solution is exposed to the atmosphere. Room temperature can constitute any temperature from about 15° C. to 35° C. The evaporation can take place until all of the solvent medium is removed leaving the purified crystals of polymorph form A. Preferably evaporation may be carried out naturally such as by slow evaporation. Depending upon the amount of the solution and its concentration, evaporation can take place over a period from three to fifteen days or longer until the solvent is completed evaporated leaving a dry solid crystalline residue which is polymorphic form A substantially free of other polymorph forms.

Polymorph form B is the anhydrous form of the acid addition salt of (+)-1-(3,4-dichlorophenyl)-3-azabicyclo[3.1.0] hexane. Polymorph form B of the acid addition salt of (+)-1-(3,4-dichlorophenyl)-3-azabicyclo[3.1.0]hexane can be prepared from a solid containing polymorph form A such as a mixture of polymorph forms A and B by dissolving the polymorph form A or the mixture of polymorph forms A and B, preferably as the hydrochloride salt, utilizing anhydrous conditions. In accordance with a preferred embodiment of the invention, this solid is in crystalline form and is re-crystallized by utilizing an anhydrous organic solvent. Any of the organic solvents mentioned hereinbefore can be utilized in their anhydrous form to produce polymorph form B. As set forth above, it is important that the re-crystallization take place under anhydrous conditions. In addition it is preferred that the removal of solvent to produce the crystalline form of polymorph B take place at elevated temperatures, i.e. from about 50° C. to 80° C., under anhydrous conditions. After crystallization of polymorph B from the solvent mixture, the solvent can be removed by filtering or decanting to leave polymorph form B substantially free of other polymorph forms. In preparing the crystallizing medium prior to removal of the solvent, the formation of the crystallizing medium containing the mixture of forms A and B for re-crystallization can take place at elevated temperatures, if desired, i.e. from 50° C. to 80° C.

Polymorph form C can be prepared from either polymorph form A or polymorph form B or mixtures thereof. Polymorph form C is prepared by extensive heating of either polymorph form A or polymorph form B, or mixtures thereof, at temperatures of at least 50° C., preferably from 60° C. to 80° C. Heating can be continued until polymorph form C substantially free of other polymorph forms is formed. This heating can, if desired, take place over long periods of time i.e. from 12 hours to 4 days of longer, until the polymorph forms of the starting material are converted to polymorph form C substantially free of other polymorph forms. The acid addition salt having the crystalline structure of polymorph form C substantially free of other polymorph forms is produced by extensive heating, usually not in the presence of a solvent, of the acid addition salts of polymorph forms A and B. The preferred acid addition salt in this preparation is the hydrochloride acid addition salt form.

The techniques set forth above also allow for the preparation of mixtures of the individual polymorph forms of the acid addition salt of (+)-1-(3,4-dichlorophenyl)-3-azabicyclo[3.1.0]hexane containing specific amounts of each of the polymorphs. In particular, mixtures of polymorph form A and either polymorph form B or polymorph form C, polymorph form B and polymorph form C, and polymorph form A, polymorph form B and polymorph form C can be readily prepared with the desired amounts of each of the polymorphs. By way of example and not of limitation, a mixture of polymorph form A and polymorph form B containing the desired amount of each polymorph can be prepared by subjecting polymorph form A substantially free of other polymorph forms and prepared as described above to the procedure for preparation of polymorph form B described above for the period of time needed to produce the desired amount of polymorph form B. By way of further example, a mixture of polymorph form A and polymorph form C containing the desired amount of each polymorph can be prepared by subjecting polymorph form A substantially free of other polymorph forms and prepared as described above to the procedure for preparation of polymorph form C described above for the period of time needed to produce the desired amount of polymorph form C. By way of additional example, a mixture of polymorph form B and polymorph form C containing the desired amount of each polymorph can be prepared by subjecting polymorph form B substantially free of other polymorph forms and prepared as described above to the procedure for preparation of polymorph form C described above for the period of time needed to produce the desired amount of polymorph form C. By way of further example, mixtures of polymorph form A and either polymorph form B or polymorph form C, polymorph form B and polymorph form C, and polymorph form A, polymorph form B and polymorph form C containing the desired amount of each polymorph can be prepared by combining the desired polymorphs substantially free of other polymorph forms and prepared as described above so that the desired mixture is obtained.

Using the techniques set forth above, mixtures containing specific percentages of the individual polymorphic forms of the acid addition salt of (+)-1-(3,4-dichlorophenyl)-3-azabicyclo[3.1.0]hexane can be obtained. For example, mixtures containing from about 10% to about 10-20%, 20-35%, 35-50%, 50-70%, 70-85%, 85-95% and up to 95-99% or greater (by weight) of polymorph form A, with the remainder of the mixture being either or both polymorph form B and polymorph form C, can be prepared. As another example, mixtures containing from about 10% to about 10-20%, 20-35%, 35-50%, 50-70%, 70-85%, 85-95% and up to 95-99% or greater (by weight) of polymorph form B, with the remainder of the mixture being either or both polymorph form A and polymorph form C, can be prepared. As a further example, mixtures containing from about 10% to about 10-20%, 20-35%, 35-50%, 50-70%, 70-85%, 85-95% and up to 95-99% or greater (by weight) of polymorph form C, with the remainder of the mixture being either or both polymorph form A and polymorph form B, can be prepared.

Additionally, many pharmacologically active organic compounds regularly crystallize incorporating second, foreign molecules, especially solvent molecules, into the crystal structure of the principal phanuacologically active compound to for in pseudopolymorphs. When the second molecule is a solvent molecule, the pseudopolymorphs can also be referred to as solvates. All of these additional forms of (+)-1-(3,4-dichlorophenyl)-3-azabicyclo[3.1.0]hexane are likewise contemplated by the present invention.

The polymorph forms A, B and C of the present invention can be prepared as acid addition salts formed from an acid and the basic nitrogen group of (+)-1-(3,4-dichlorophenyl)-3-azabicyclo[3.1.0]hexane. Suitable acid addition salts are formed from acids, which faun non-toxic salts, examples of which are hydrochloride, hydrobromide, hydroiodide, sulphate, hydrogen sulphate, nitrate, phosphate, and hydrogen phosphate. Examples of pharmaceutically acceptable addition salts include inorganic and organic acid addition salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; organic acid salts such as acetate, citrate, lactate, succinate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, aspargenate, glutamate, tartrate, gluconate and the like. The hydrochloride salt formed with hydrochloric acid is an exemplary useful salt.

The above individual polymorph forms and mixtures of polymorph forms of the acid addition salt of (+)-1-(3,4-dichlorophenyl)-3-azabicyclo[3.1.0]hexane can be administered to human patients in the same manner as the previously known forms of (+)-1-(3,4-dichlorophenyl)-3-azabicyclo[3.1.0]hexane. Suitable routes of administration for the above individual polymorph forms and mixtures of polymorph foams of an acid addition salt of (+)-1-(3,4-dichlorophenyl)-3-azabicyclo[3.1.0]hexane include, but are not limited to, oral, buccal, nasal, pulmonary, aerosol, topical, transdermal, mucosal, injectable, slow release and controlled release delivery, although various other known delivery routes, devices and methods can likewise be employed. Useful parenteral delivery methods include, but are not limited to, intravenous, intramuscular, intraperitoneal, intraspinal, intrathecal, intracerebroventricular, intraarterial, and subcutaneous injection.

Suitable effective unit dosage amounts for the above individual polymorphic forms and mixtures of polymorphic forms of an acid addition salt of (+)-1-(3,4-dichlorophenyl)-3-azabicyclo[3.1.0]hexane for mammalian subjects may range from about 1 to 1200 mg, 50 to 1000 mg, 75 to 900 mg, 100 to 800 mg, or 150 to 600 mg. In certain embodiments, the effective unit dosage will be selected within narrower ranges of, for example, about 10 to 25 mg, 30 to 50 mg, 75 to 100 mg, 100 to 150 mg, 150 to 250 mg or 250 to 500 mg. These and other effective unit dosage amounts may be administered in a single dose, or in the form of multiple daily, weekly or monthly doses, for example in a dosing regimen comprising from about 1 to 5, or 2-3, doses administered per day, per week, or per month. In exemplary embodiments, dosages of about 10 to 25 mg, 30 to 50 mg, 75 to 100 mg, 100 to 200 (anticipated dosage strength) mg, or 250 to 500 mg, are administered one, two, three, or four times per day. In more detailed embodiments, dosages of about 50-75 mg, 100-150 mg, 150-200 mg, 250-400 mg, or 400-600 mg are administered once, twice daily or three times daily. In alternate embodiments, dosages are calculated based on body weight, and may be administered, for example, in amounts from about 0.5 mg/kg to about 30 mg/kg per day, 1 mg/kg to about 15 mg/kg per day, 1 mg/kg to about 10 mg/kg per day, 2 mg/kg to about 20 mg/kg per day, 2 mg/kg to about 10 mg/kg per day or 3 mg/kg to about 15 mg/kg per day.

Using the routes and methods of administration and dosage amounts described hereinabove and the dosage forms described hereinbelow, the individual polymorph forms and mixtures of polymorph forms of the present invention can be used for the prevention and treatment of various diseases and conditions in humans. By way of example and not of limitation, in the case of depression, this is accomplished by administering to a patient in need of said treatment who is suffering from depression a composition containing one of the above polymorph forms substantially free of other polymorph forms or mixtures of polymorphs and an inert carrier or diluent, said composition being administered in an effective amount to prevent or treat said depression. In accordance with this invention, (+)-1-(3,4-dichlorophenyl)-3-azabicyclo[3.1.0]hexane, either as a polymorph form substantially free of other polymorph forms or as a mixture of polymorph forms, is administered in an effective amount to prevent or treat depression. Any effective amount of such polymorph form substantially free of other polymorph forms or mixtures of polymorph forms needed to prevent or treat depression can be utilized in this composition. In general, in the case oral dosage forms, dosages of from about 0.5 mg/kg to about 5.0 mg/kg of body weight per day are used. However the amount of such polymorph form substantially free of other polymorph forms or mixtures of polymorph forms in the oral unit dose to be administered will depend to a large extent on the condition of depression and the weight of the patient and of course be subject to the physician's judgment. In accordance with this invention, the oral unit dosage form containing the given polymorph form substantially free of other polymorph forms or mixtures of polymorph forms can be preferably administered at a dosage of from about 30 mg to 300 mg per day, more preferably from about 50 mg to about 200 mg per day, administered once or twice during the day or as needed.

The present invention includes pharmaceutical dosage forms for the above individual polymorph forms and mixtures of polymorph forms of an acid addition salt of (+)-1-(3,4-dichlorophenyl)-3-azabicyclo[3.1.0]hexane. Such pharmaceutical dosage forms may include one or more excipients or additives, including, without limitation, binders, fillers, lubricants, emulsifiers, suspending agents, sweeteners, flavorings, preservatives, buffers, wetting agents, disintegrants, effervescent agents and other conventional excipients and additives. The compositions of the present invention can thus include any one or a combination of the following: a pharmaceutically acceptable carrier or excipient: other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to patients without causing deleterious side effects or interactions with the active agent.

As previously noted, polymorph form A is a thermodynamically stable polymorph of an acid addition salt of (+)-1-(3,4-dichlorophenyl)-3-azabicyclo[3.1.0]hexane. Therefore, it is preferred that polymorph form A be used in pharmaceutical dosage forms without the presence of other geometrical, optical and polymorphic isomers of (+)-1-(3,4-dichlorophenyl)-3-azabicyclo[3.1.0]hexane. However, polymorph forms B and C can also be included in pharmaceutical product formulations with less positive results concerning formulation and stability.

If desired, the individual polymorph forms or mixtures of polymorph forms of the present invention can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps.

The individual polymorph forms or mixtures of polymorph forms of the present invention can be formulated and administered in oral dosage form, optionally in combination with a carrier or other additive(s). Suitable-carriers common to pharmaceutical formulation technology include, but are not limited to, microcrystalline cellulose, lactose, sucrose, fructose, glucose, dextrose, other sugars, di-basic calcium phosphate, calcium sulfate, cellulose, methylcellulose, cellulose derivatives, kaolin, mannitol, lactitol, maltitol, xylitol, sorbitol, other sugar alcohols, dry starch, dextrin, maltodextrin, other polysaccharides, or mixtures thereof.

Exemplary oral unit dosage forms for use in the present invention include tablets, capsules, powders, solutions, syrups, suspensions and lozenges, which may be prepared by any conventional method of preparing pharmaceutical oral unit dosage forms. Oral unit dosage forms, such as tablets, may contain one or more of the conventional, pharmaceutically acceptable additional formulation ingredients, including but not limited to, release modifying agents, glidants, compression aides, disintegrants, effervescent agents, lubricants, binders, diluents, flavors, flavor enhancers, sweeteners and preservatives. These ingredients are selected from a wide variety of excipients known in the pharmaceutical formulation art. Depending on the desired properties of the oral unit dosage form, any number of ingredients may be selected alone or in combination for their known use in preparing such dosage forms as tablets.

Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants. The aforementioned effervescent agents and disintegrants are useful in the formulation of rapidly disintegrating tablets known to those skilled in the art. These typically disintegrate in the mouth in less than one minute, and often in less than thirty seconds. By effervescent agent is meant a couple, typically an organic acid and a carbonate or bicarbonate.

The following examples illustrate certain embodiments of the present invention, and are not to be construed as limiting the present disclosure.

EXAMPLES

Example 1

This example is directed to preparing the hydrochloride salt of (+)-1-(3,4-dichlorophenyl)-3-azabicyclo[3.1.0]hexane from the free base of (+)-1-(3,4dichlorophenyl)-3-azabicyclo[3.1.0]hexane and to demonstrate that this method produced a mixture of polymorph form A and polymorph form B.

Approximately 250 mg of the free base of (+)-1-(3,4-dichlorophenyl)-3-azabicyclo[3.1.0]hexane was dissolved in 400 mL 95:5 (v/v) hexane/isopropanol (with 0.05% diethylamine). The solution was evaporated under a nitrogen stream on a stir plate set at approximately 70° C., concentrating the sample to a clear gel. This gel was dissolved in 50 mL ethyl acetate and dried under a nitrogen stream, yielding a thin, clear to off-white (tint of yellow), milky residue. This residue was dissolved in 7 mL diethyl ether, and 7 mL HCl saturated diethyl ether was added; chunks of white solid were precipitated immediately. This solid was recovered through vacuum filtration and washed with 19 mL diethyl ether. The filtered solid appeared dry. The (+)-1-(3,4-dichlorophoyl)-3-azabicyclo[3.1.0]hexane hydrochloride salt was recovered (162.5 mg), resulting in a yield of 55.7%.

XRPD analysis and Raman spectroscopy performed as described above indicated that both the starting material (free base) and end product (hydrochloride salt) constituted a mixture of polymorph form A and polymorph form B. Both the starting material and end product were observed to contain approximately 50% (by weight) of each polymorph. There was only a minor difference in the % of these polymorphs in the starting material and in the final product.

Example 2

Stability Studies on the End Product of Example 1

Duplicate samples of the hydrochloride salt of (+)-1-(3, 4dichlorophenyl)-3-azabicyclo[3.1.0]hexane produced in Example 1 and containing a 50% (by weight) mixture of polymorph form A and polymorph form B were placed on informal stability to test storage in desiccators placed at ambient temperature and at 50° C. in a programmable heating bloc. The samples were examined after 1 week and while both samples contained mixtures of polymorph form A and polymorph form B, the ratios observed showed some conversion of forms. The mixture subjected to ambient temperature was observed to contain 40% (by weigh) of polymorph form A and 60% (by weight) of polymorph form B (as determined by XPRD analysis?). This result was confhined by Raman spectroscopy. Subsequent XRPD analysis of the sample stored in a 50° C. programmable heating block showed about 50% (by weight) of polymorph form A and 50% (by weight) of polymorph form C after 17 days of storage.

Example 3

Method of Manufacture of (+)-1-(3,4-dichlorophenyl)-3-azabicyclo[3.1.0]hexane hydrochloride Step 1: Synthesis of α-bromo-3,4-dichlorophenylacetic acid methyl ester 100 kg 3,4-dichlorophenylacetonitrile was added in portions over 1.25 hours to a mixture of 12 kg water and 140 kg 98% sulfuric acid. Exotherm was allowed to 65° C. maximum, and the reaction mix was maintained at 60-65° C. for 30 minutes. After cooling to 50° C., 80 kg methanol was slowly added over 25-30 minutes. The mixture was warmed to 92-98° C., and maintained at this temperature for an additional three hours. After cooling to 35° C., the reaction mixture was quenched into an agitated mixture (precooled to 0-5° C.) of 150 L ethylene dichloride and 250 L water. The reactor and lines were washed with water into the quench mix, which was agitated 5 minutes and allowed to stratify. The lower organic phase was separated, and the aqueous phase washed with 2×150 L ethylene dichloride. The combined organic phases were washed with 100 L water and then with aqueous sodium carbonate (3 kg sodium carbonate in 100 L water). The solution of crude ester was azeotropically "dried" in vacuo at 60-620 C, resulting in the collection of 100 L ethylene dichloride. A theoretical yield was assumed without isolation and the solution was used "as is" in the following bromination reaction.

A mixture of the solution (line-filtered) of crude methyl 3,4-dichlorophenylacetate (from above) and 88 kg 1,3-dibromo-1,3-dimethylhydantoin (DBDMH) was warmed to 80° C., and a solution of 2.5 kg VAZO 52 in 15 L ethylene dichloride was added portion wise over a 5 hour period, maintaining 85-90° C. (under reflux). An additional 8.8 kg DBDMH was then added, and a solution of 0.5 kg VAZO 52 in 4 L ethylene dichloride was added portion wise over a 2.5 hour period, maintaining 85-90° C. (under reflux). Heating was then discontinued, and 350 L water was added with agitation. The mixture was allowed to stratify, the lower organic phase was separated and the aqueous phase was washed with 50 L ethylene dichloride. The combined organic phases were washed with aqueous thiosulfate (5.0 kg sodium thiosulfate in 150 L water), aqueous sodium carbonate (2.5 kg sodium carbonate in 150 L water), and dilute hydrochloric acid (5.4 L 32% HCl in 100 L water). The organic phase was line-filtered and distilled in vacuo to "dryness" (full vacuum to 83° C.). Residual ethylene dichloride was chased with 20 kg toluene (full vacuum at 83° C.). The crude α-bromo-3,4-dichlorophenylacetic acid methyl ester was taken up in 82 kg toluene, cooled to 40° C., and discharged to steel drums. The product was not isolated, and was used "as is" in Step 2. A theoretical yield was assumed for calculation purposes.

Step 2: Synthesis of 1-(3,4-dichlorophenyl-1,2-cyclopropane-dicarboxylic acid dimethyl ester The crude α-bromo-3,4-dichlorophenylacetic acid methyl ester from Step 1 was mixed well with 55.6 kg methyl acrylate, and then the mixture was added to a precooled (−2° C.) mixture of 54.4 kg potassium methoxide in 500 L toluene (argon blanket) over 5.5 hours with good agitation and maintained at <+10° C. After standing overnight (5 psig argon) with brine cooling (−5° C.), the cold reaction mixture was quenched into a mix of 250 L water and 30 kg 32% hydrochloric acid with good agitation. 200 L water and 2.5 kg potassium carbonate were added to the mixture with good agitation for an additional 30 minutes. After stratification, the lower aqueous phase was separated, and 150 L water and 1.0 kg potassium carbonate were added to the organic phase. The mixture was agitated 5 minutes and stratified. The lower aqueous phase was separated and discarded, as well as the interfacial emulsion, and the organic phase was washed with 100 L water containing 1 L 32% hydrochloric acid. After stratification and separation of the lower aqueous phase, the organic phase was line-filtered and distilled in vacuo to "dryness" (full vacuum at 65° C.). To the hot residue was added 70 kg methanol with agitation. The mix was cooled (seeding at +10° C.) to −5° C. and maintained at this temperature overnight. The cold thick suspension was suction-filtered (Nutsche), and the cake of 1-(3,4-dichlorophenyl)-1,2-cyclopropane-dicarboxylic acid dimethyl ester was suction dried, washed with 2×20 L hexane, suction dried for 30 minutes and air-dried on paper (racks) for 2 days at ambient conditions.

To the methanolic liquors was added 50 kg caustic soda flake portion wise over 8 hours with good agitation. After gassing and the slow exotherm (60° C. maximum) ceased, the heavy suspension was held at 50° C. for 1 hour. 100 L isopropanol was slowly added over 10 minutes, and then the mixture was agitated slowly overnight at ambient conditions. The solids were suction-filtered (Nutsche) and reslurried with 80 L methanol. The resulting 1-(3,4-dichlorophenyl)-1,2-cyclopropane-dicarboxylic acid disodium salt was suctioned-filtered (Nutsche), washed with methanol (40 L), suction dried for 1 hour and air-dried on paper (racks).

Step 3: Synthesis of 1-(3,4-dichlorophenyl)-1,2-cyclopropane-dicarboxylic acid A suspension of 42.0 kg 1-(3,4-dichlorophenyl)-1,2-cyclopropane-dicarboxylic acid disodium salt (from Step 2) and 120 L deionized water was warmed to 30-35° C., and the solution was line-filtered and neutralized with 30 kg 32% hydrochloric acid to precipitate the free dicarboxylic acid. 120 kg ethyl acetate was added, and the mix warmed to 40-50° C. to effect solution. The lower aqueous phase was separated and washed with 20 kg ethyl acetate. The combined organic extracts were washed with saturated sodium chloride (3 kg in 30 L water) and then distilled in vacuo to "dryness" (full vacuum to 70° C.). 60 kg ethylene dichloride was added to the warm residue, and the solution cooled with slow agitation at −5° C. overnight. Residual ethyl acetate was distilled (full vacuum to 43° C.) to yield a thick suspension, which was then cooled with full vacuum to −5° C. over a 2.5 hour period and then suction-filtered (Nutsche). The 1-(3,4-dichlorophenyl)-1,2-cyclopropane-dicarboxylic acid cake was washed with cold ethylene dichloride (2×5 L), followed by ambient ethylene dichloride (4×5 L). The dicarboxylic acid product was suction dried for 15 minutes and air-dried on paper (racks).

A mixture of 31.0 kg 1-(3,4-dichlorophenyl)-1,2-cyclopropane-dicarboxylic acid dimethyl ester (from Step 2), 40 L water, 35 kg methanol and 18.0 kg 50% caustic soda was warmed to 70-75° C. (under reflux) and maintained at 70-75° C. for 1.5 hours. 10 L water was then added, and the mixture was kept at 75-77° C. for an additional 2 hours. Methanol was slowly distilled off in vacuo to 70° C. to give a heavy suspension, which was then mixed with 80 L water to effect solution. The free dicarboxylic acid was precipitated with 31 kg of 32% hydrochloric acid and extracted with 100 kg ethyl acetate. The lower aqueous phase was separated and washed with 20 kg ethyl acetate. The combined organic phases were washed with 50 L water, and then saturated aqueous sodium chloride. Distillation in vacuo to 80° C. with full vacuum yielded a concentrate of 1-(3,4-dichlorophenyl)-1,2-cyclopropane-dicarboxylic acid, which was used "as is" for the next step, cyclization to the imide. A quantitative yield from the diester was assumed for calculation purposes.

Step 4: Synthesis and Recrystallization of 1-(3,4-dichlorophenyl)-3-azabicyclo[3.1.0]hexane-2,4-dione The slurry of 1-(3,4-dichlorophenyl)-1,2-cyclopropane-dicarboxylic acid (from Step 3) was added to 45.6 kg warm (68° C.) formamide, and residual ethyl acetate was distilled with full vacuum at 68-73° C. An additional 14.4 kg formamide was added to the mixture, followed by 11.2 kg of the dicarboxylic acid (derived from the disodium salt, Step 3). An argon blanket on the mixture was maintained for the following operation. The mixture was agitated 15 minutes at 73-75° C. to effect a complete solution, and then heated over a 1 hour period to 140-145° C. and maintained at this temperature for an additional 2.25 hours. Heating was discontinued, and the mixture was cooled to 70° C. and 10 L water containing 20 ml 32% HCl was slowly added over 30 minutes. The mixture was seeded and crystallization commenced. An additional 20 L water was slowly added to the heavy suspension over a 2 hour period. After standing overnight at ambient conditions, the mixture was agitated for 1.25 hours at ambient temperature and then suction-filtered (Nutsche). The cake of crude 1-(3,4-dichlorophenyl)-3-azabicyclo-[3.1.0]hexane-2,4-dione was washed with water (3×20 L), suction dried for 30 minutes and air-dried on paper (racks) for 2 days under ambient conditions.

A mixture of 37 kg crude, damp 1-(3,4-dichlorophenyl)-3-azabicyclo-[3.1.0]hexane-2,4-dione (from Step 4, above) and 120 L toluene was warmed to 75-80° C. to effect solution. After stratification and separation of the residual water (3.3 kg), 1 kg Darco G-60 activated carbon (American Norit Co.) (suspended in 5 L toluene) was added. The mixture was agitated at 80° C. for 30 minutes and then pressure filtered through a preheated Sparkler (precoated with filteraid), polishing with a 10 μm in-line filter. The clear light yellow solution was concentrated in vacuo at 75-80° C. to 100 L final volume and slowly cooled, with seeding at 70° C. The heavy crystalline suspension was cooled to −5° C., held 30 minutes at this temperature and suction-filtered (Nutsche). The cake of purified 1-(3,4-dichlorophenyl)-3-azabicyclo-[3.1.0]hexane-2,4-dione was washed with 2×10 L cold (−10° C.) toluene, and then 2×20 L hexane. After suction drying for 30 minutes, the 2,4-dione product was dried in vacuo (≤62° C.).

Step 5: Synthesis and Purification of (±)-1-(3,4-Dichlorophenyl)-3-azabicyclo[3.1.0]hexane hydrochloride BH3-THF complex is charged into a 2 L addition funnel (9×2 L, then 1×1.5 L) and drained into a 50 L flask.

1000 g of (±)-1-(3,4 dichlorophenyl)-3-azabicyclo[3.1.0]-hexane-2,4-dione is dissolved in 2 L of THF and added to the BH3-THF dropwise over a period of 2 hours. The reaction mixture is heated to reflux and held at this temperature overnight. The mixture is then cooled to <10° C., adjusted to pH 2 with the addition of 1200 mL of 6N HCl dropwise at <20° C., and stirred for a minimum of 1 hour.

The reaction mixture is then transferred to a 10 L Buchi flask, concentrated to a milky white paste, and transferred again to a 5-gallon container. The mixture is diluted with 4 L of cold water and adjusted to pH 10 with 2000 mL of a 25% sodium hydroxide solution. A temperature of <20° C. is maintained. Following this, 4.5 L of ethyl acetate is added and the mixture is stirred for 15 minutes. The solution is then filtered through a 10 inch funnel with a filter cloth and washed with ethyl acetate (2×250 mL).

The filtrate is then transferred into a 40 L separatory funnel and the phases are allowed to separate. Each phase is then drained into separate 5-gallon containers. The aqueous layer is returned to the 40 L separatory funnel and extracted with ethyl acetate (2×2 L). The organic phases are combined. The aqueous layer is discarded.

250 g of magnesium sulfate and 250 g of charcoal are added to the combined organics and the mixture is stirred well. The solution is then filtered through an 18.5 cm funnel using a filter pad and washed with ethyl acetate (2×250 mL). The filtrate is then transferred to a 10 L Buchi flask and concentrated to dryness. The resulting yellowish oil is diluted with ethyl acetate (2.25 mL/g).

HCl gas is bubbled through a 12 L flask containing 10 L of ethyl acetate to make an approximately 2.3 M solution of HCl/ethyl, acetate. This HCl/ethyl acetate solution is added to the oil dropwise at a rate that maintains a temperature of <20° C. using an ice/water bath. The solution is then stirred at <10° C. for a minimum of 2 hours in the ice/water bath. The material is chilled in a cold room overnight.

The resulting solids are then filtered through a 10 inch funnel utilizing a filter cloth and washed with ethyl acetate (2×200 mL) and ethyl ether (3×500 mL). The product, crude (±)-1-(3,4-Dichlorophenyl)-3-azabicyclo[3.1.0]-hexane hydrochloride, is then transferred to Pyrex drying trays and dried for 4 hours.

1900 g of crude (±)-1-(3,4-dichlorophenyl)-3-azabicyclo[3.1.0]hexane hydrochloride from above, and 15.2 L of isopropyl alcohol are charged to a 22 L flask. The mixture is heated to dissolve all material.

The material is then filtered through a 18.5 cm funnel utilizing a filter pad and transferred to a 22 L flask. The solution is then stirred at room temperature for 1 hour. The solution is then chilled to 4° C. with an ice/water bath and stirred for 3.75 hours. The product is then placed in a cold room overnight.

The solids are then filtered through a 13 inch filter using a filter cloth and washed with ethyl ether (3×633 mL). The product is then air dried for 2 hours.

The product, pure (±)-1-(3,4-dichlorophenyl)-3-azabicyclo[3.1.0]hexane hydrochloride, is transferred to clean Pyrex drying trays and dried to constant weight.

Step 6: Resolution of (±)-1-(S3,4-dichlorophenyl)-3-azabicyclor[3.1.0]hexane hydrochloride into (+)-1-(3,4-dichlorophenyl)-3-azabicyclo[3.1.0]hexane hydrochloride In a 50 gallon reactor containing 60 L of 15% NaOH, 13.6 kg of pure (±)-1-(3,4dichlorophenyl)-3-azabicyclo[3.1.0] hexane hydrochloride (from Step 5, above) is added while keeping the temperature constant at approximately 20° C. Once the addition of (±)-1-(3,4-dichlorophenyl)-3-azabicyclo[3.1.0]hexane hydrochloride is complete, the reaction mixture is allowed to stir at room temperature for a minimum of 8 hours.

40 L of ethyl acetate is added to the reactor and the two phase mixture is stirred until a clear solution is obtained (approximately 2 hours). The phases are allowed to separate and the organic layer is transferred to another 50 gallon reactor. The remaining aqueous layer is extracted with ethyl acetate (6×6 L). All organic phases are combined into the 50-gallon reactor. The organic phase is dried and decolorized by the addition of 4000 g magnesium sulfate and 250 g of charcoal. The mixture is then filtered through an in-line filter. The filtrate is transferred via in-line filter to a 50-gallon reactor.

In a separate 50-gallon reactor, 23,230 g of L-(−)-dibenzoyl tartaric acid is dissolved with stirring (approximately 30 minutes) in 71 L of methanol. The dissolution is assisted with heating if necessary.

The L-(−)-dibenzoyl tartaric acid solution in methanol is added via addition funnel to the reactor containing the filtrate, over a period of approximately 1 hour, maintaining the temperature at 15-25° C., After the addition is complete the mixture is stirred for approximately 16 hours at 15-25° C. Following stirring, 50 L of methanol is added to the mixture and it is stirred again for 30 additional minutes. The resulting solids are filtered onto a plate filter. The solids are then washed with methanol (3×5 L) and pressed dry. The crude solids are weighed and transferred to a 50-gallon reactor to which 80 L of methanol is added. The mixture is heated to reflux and stirred at reflux for approximately 30 minutes. The mixture is then cooled to 15-20° C. and stirred at this temperature for approximately 2 hours. The resulting solids are filtered onto a plate filter using a polypropylene filter cloth. The cake is washed with methanol (3×5 L) and pressed dry. The solids are transferred to a tarred 5-gallon container and weighed (yield ~20 kg).

The solids are then added (over a period of approximately 1 hour) to a 50 gallon reactor vessel containing 60 L of 15% NaOH while maintaining the temperature at approximately 20° C. Once the addition of the solids is complete the reaction mixture is stirred for approximately 19 hours.

40 L of ethyl acetate is charged to the reactor, while maintaining the temperature at ≤3.5° C. and the two phase mixture is stirred until a clear solution is obtained (approximately 2 hours). The phases are allowed to separate and the organic layer is transferred to another 50 gallon reactor. The remaining aqueous layer is extracted with ethyl acetate (6×6 L). All organic phases are combined into the 50-gallon reactor. 5000 g of magnesium sulfate is then added to the organic phase. The mixture is then filtered through an in-line filter. The filtrate is transferred via in-line filter to a 50-gallon reactor. The filtrate is concentrated to a total volume of 20-30 L.

In a 22 L three neck round bottom flask, HCl gas is bubbled through 12 L of ethyl acetate to make an approximately 2.3 M solution of HCl/ethyl acetate. After titration assay, the solution is adjusted to exactly 2.3 M by adding either ethyl acetate or HCl gas.

8.2 L of the 2.3 M solution of HCl/ethyl acetate is added (over a period of approx. 1.5 hours) to the filtrate (above), maintaining the temperature at ≤20° C. and ensuring that a pH of 2 is obtained. Once the addition is complete, the mixture is stirred at 0 to −5° C. for a period of 16 hours.

The resulting solids, crude (+)-1-(3,4-dichlorophenyl)-3-azabicyclo[3.1.0]hexane hydrochloride, are filtered onto a plate filter using a polypropylene filter cloth. The solids are then washed with ethyl acetate (2×2 L), acetone (2×2 L) and ethyl ether (2×2 L) and dried under vacuum. The material is transferred to a tarred 5-gallon polyethylene container and weighed.

Step 6a: Recrystallization of (+)-1-(3,4-dichlorophenyl)-3-azabicyclo[3.1.0]hexane hydrochloride from isopropanol The solids (from Step 6, above) are transferred to a 50-gallon reactor and isopropanol is added (8-10 mL/g of solid). The mixture is heated to reflux. The solution is filtered through an in-line filter into another 50 gallon reactor. The solution is cooled to 0 to −5° C. and maintained at this temperature with stirring for approximately 2 hours. The resulting solids are filtered onto a plate filter using a polypropylene filter cloth. The solids are then washed with ethyl acetate (2×2 L), acetone (2×2 L) and ethyl ether (2×2 L). The solids are dried under vacuum.

The product, (+)-1-(3,4-dichlorophenyl)-3-azabicyclo[3.1.0]hexane hydrochloride, is transferred into clean, tarred drying tray(s). The tray(s) are placed in a clean, vacuum drying oven. The product is dried at 50° C. to constant weight. The material is dried for a minimum of 12 hours at <10 mm Hg. This product was a mixture of polymorph form A and polymorph form B, with each polymorph present in the mixture in an amount of about 50% by weight. This product was used as the starting material for Examples 4 through 8 below.

Example 4

The 50% by weight mixture of polymorph form A and polymorph form B of the hydrochloride salt of (+)-1-(3,4-dichlorophenyl)-3-azabicyclo[3.1.0]hexane (54 mg) was dissolved in 12 ml of acetonitrile and water. Approximately half of this stock solution was then filtered through a 0.2:m nylon syringe filter into a clean vial. The vial was covered with aluminum foil punctured with a pinhole and left in a fume hood under ambient conditions for slow evaporation. After allowing the solvent in the vial to evaporate, which occurred in about four days, a crystal residue was obtained which was the pure polymorph form A form of the hydrochloride salt of (+)-1-(3,4-dichlorophenyl)-3-azabicyclo[3.1.0]hexane as demonstrated by Raman spectroscopy and XRPD analysis as described above The same pure crystalline form was also obtained with other solvents prepared using the same method, such as acetone, 2-butanol, dichloromethane, ethanol, methanol, nitromethane, isopropanol and tetrahydrofuran. These solvents also contained water.

Example 5

68 mg of the 50% by weight mixture of polymorph form A and polymorph form B of the hydrochloride salt of (+)-1-(3,4-dichlorophenyl)-3-azabicyclo[3.1.0]hexane was dissolved in 3.4 ml of ethyl ether:ethanol (1:1 ratio) solvent mixture. The resulted solution was filtered through a 0.2:m nylon syringe filter into a clean vial. Solid samples were collected by rotary evaporation of the solvents under vacuum. The solids were than dried under vacuum at ambient temperature to produce pure polymorph form B crystals of the hydrochloride salt of (+)-1-(3,4-dichlorophenyl)-3-azabicyclo[3.1.0]hexane as demonstrated by Raman spectroscopy and XRPD analysis as described above.

Example 6

51 mg of the 50% by weight mixture of polymorph form A and polymorph form B of the hydrochloride salt of (+)-1-(3,4-dichlorophenyl)-3-azabicyclo[3.1.0]hexane was weighed into a vial. The vial was covered with aluminum foil perforated with pinholes and placed in an oven at 80° C. for 4 days to produce the pure polymorph C crystals of the hydrochloride salt of (+)-1-(3,4-dichlorophenyl)-3-azabicyclo[3.1.0]hexane as demonstrated by Raman spectroscopy and XRPD analysis as described above.

Example 7

Preparation of Polymorph Form B 40 mg samples of the 50% by weight mixture of polymorph form A and polymorph foam B of the hydrochloride salt of (+)-1-(3,4-dichlorophenyl)-3-azabicyclo[3.1.0]hexane were mixed with 0.5 mL of anhydrous acetonitrile to produce a concentration of about 80-100 mg/mL and the resulting samples were stirred at various temperatures between 50° C. and 80° C. for various periods of time (some for 4 days and 6 days at about 50° C. and some for 1 day at about 80° C.). The resulting samples were each mixtures of a clear liquid and some solid. The clear liquid was decanted off, and the remaining solid was vacuum dried at ambient temperature for 1 hour to 2 days (50° C. sample), or 6 days (80° C. sample) to afford pure crystalline polymorph form B. All samples produced the pure polymorph form B crystals of the hydrochloride salt of (+)-1-(3,4-dichlorophenyl)-3-azabicyclo[3.1.0]hexane as demonstrated by Raman spectroscopy and XRPD analysis as described above.

Example 8

Preparation of Polymorph Form A 20 mg samples of the 50% by weight mixture of polymorph form A and polymorph form B of the hydrochloride salt of (+)-1-(3,4-dichlorophenyl)-3-azabicyclo[3.1.0]hexane were dissolved in 0.5 ml of aqueous ethanol. Other samples were prepared by dissolving 20 mg of this mixture in 0.5 mL of water. Both solutions were filtered through a 0.2 micron nylon filter. Both filtered solutions were then allowed to evaporate under ambient conditions, some samples partially covered and other samples completely uncovered. After 6 days, both the uncovered and partially covered ethanol solution samples evaporated. After 7 days, the uncovered water solutions evaporated. After 15 days, the partially covered water solutions evaporated. For each sample, after the solvent (either aqueous ethanol or water) evaporated completely, 20 mg of dry solid residue was left. The solid in all samples thus produced was the pure polymorph form A crystals of the hydrochloride salt of (+)-1-(3,4-dichlorophenyl)-3-azabicyclo[3.1.0]hexane as demonstrated by Raman spectroscopy and XRPD analysis as described above.

The invention claimed is:

1. Crystalline (+)-1-(3,4-dichlorophenyl)-3-azabicyclo[3.1.0]hexane hydrochloride, wherein the (+)-1-(3,4-dichlorophenyl)-3-azabicyclo[3.1.0]hexane hydrochloride exhibits at least one of:
   an X-ray powder diffraction pattern, as measured with Cu Kα radiation at crystal sizes of from about 10 to 40 microns, comprising peaks at about the following °2θ (degree) values:
   17.14;
   19.62;
   21.96;
   24.52;
   and
   26.74, or
   a Raman spectrum comprising peaks at about the following wavenumbers (cm$^{-1}$):
   762;
   836;
   921;
   959;
   1393;

1597;
2890;
2982;
and
3064, substantially free of other geometric and optical isomers and polymorphic forms thereof.

* * * * *

UNITED STATES PATENT AND TRADEMARK OFFICE
CERTIFICATE OF CORRECTION

PATENT NO. : 8,765,801 B2   Page 1 of 1
APPLICATION NO. : 13/366209
DATED : July 1, 2014
INVENTOR(S) : Eric J. Hagen and Kevin Halloran It is certified that error appears in the above-identified patent and that said Letters Patent is hereby corrected as shown below:

In the Claims

Claim 1, column 22, lines 47-50, "Crystalline (+)-1-(3,4-dichlorophenyl)-3-azabicyclo[3.1.0]hexane hydrochloride, wherein the (+)-1-(3,4-dichlorophenyl)-3-azabicyclo[3.1.0]hexane hydrochloride exhibits at least one of:" should read:

-- Polymorph form A of (+)-1-(3,4-dichlorophenyl)-3-azabicyclo[3.1.0]hexane hydrochloride, wherein the polymorph exhibits at least one of: --

Signed and Sealed this
Fourteenth Day of April, 2015

Michelle K. Lee
*Director of the United States Patent and Trademark Office*